United States Patent [19]

Blank

[11] Patent Number: 5,169,625
[45] Date of Patent: * Dec. 8, 1992

[54] ANTIMICROBIAL WATER SOLUBLE SUBSTRATES

[75] Inventor: Lynne M. B. Blank, Brighton, N.Y.

[73] Assignee: Dow Corning Corporation, Midland, Mich.

[*] Notice: The portion of the term of this patent subsequent to May 1, 2007 has been disclaimed.

[21] Appl. No.: 391,910

[22] Filed: Aug. 10, 1989

Related U.S. Application Data

[63] Continuation of Ser. No. 230,945, Aug. 11, 1988, Pat. No. 4,921,701.

[51] Int. Cl.$^5$ .......................... A61K 7/32; A61K 7/34; A61K 7/36; A61K 7/38
[52] U.S. Cl. ....................................... 424/65; 424/66; 424/67; 424/68
[58] Field of Search .................... 424/401, 66, 67, 68, 424/65, 493, 405, 63, 78; 514/63; 428/05; 604/360, 359

[56] References Cited

U.S. PATENT DOCUMENTS 4,605,554  8/1986  Prussin et al. .......................... 424/66

FOREIGN PATENT DOCUMENTS 59-223371  12/1984  Japan .
60-162870   8/1985  Japan .
60-52773   12/1985  Japan .
62-015308   1/1987  Japan .
2076290    12/1981  United Kingdom .................. 424/66

*Primary Examiner*—Lester L. Lee
*Attorney, Agent, or Firm*—Jim L. DeCesare

[57] ABSTRACT

An antimicrobial water soluble substrate is formed by combining a silane, generically a quaternary ammonium salt form of a silane, with a water soluble powder selected from the group consisting of antiperspirant salts, starches, clays, and sugars. When the substrate is dissolved in water, the silane is released for redeposition.

3 Claims, No Drawings

ANTIMICROBIAL WATER SOLUBLE SUBSTRATES

This is a continuation of co-pending application Ser. No. 07/230,945 filed on Aug. 11, 1988 now U.S. Pat. No. 4,921,701.

BACKGROUND OF THE INVENTION

This invention relates to antimicrobial agents and more particularly to new water soluble substrates including quaternary ammonium salt compounds having biological activity.

Antimicrobial agents are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone quaternary ammonium salt compounds are well known as exemplified by U.S. Pat. No. 3,560,385, issued Feb. 2, 1971, and the use of such compounds as antimicrobial agents is taught, for example, in a wide variety of patents such as U.S. Pat. Nos. 3,730,701, issued May 1, 1973, and 3,817,739, issued Jun. 18, 1974, where the compounds are used to inhibit algae; 3,794,736, issued Feb. 26, 1974, and 3,860,709, issued Jan. 14, 1975, where they are employed for sterilizing or disinfecting a variety of surfaces and instruments; 3,865,728, issued Feb. 11, 1975, where the compounds are used to treat aquarium filters; 4,259,103, issued Mar. 31, 1981; and in British Patent No. 1,386,876, of Mar. 12, 1975. Published unexamined European Application No. 228464 of Jul. 15, 1987, teaches that microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366, issued Aug. 4, 1981. In U.S. Pat. No. 4,504,541, issued Mar. 12, 1985, an antimicrobial fabric is disclosed which is resistant to discoloration and yellowing by treatment of the fabric with a quaternary ammonium base containing an organosilicone. U.S. Pat. No. 4,615,937, issued Oct. 7, 1986, as well as its companion U.S. Pat. No. 4,692,374, issued Sep. 8, 1987, relate to wet wiper towelettes having an antimicrobial agent substantive to the fibers of the web and being an organosilicon quaternary ammonium compound. In a series of Burlington Industries, Inc. U.S. Pat. Nos. 4,408,996, issued Oct. 11, 1983, 4,414,268, issued Nov. 8, 1983, 4,425,372, issued Jan. 10, 1984, and 4,395,454, issued Jul. 26, 1983, such compounds are disclosed to be useful in surgical drapes, dressings, and bandages. This same assignee also discloses these compounds as being employed in surgeons' gowns in U.S. Pat. Nos. 4,411,928, issued Oct. 25, 1983, and 4,467,013, issued Aug. 21, 1984. Organosilicon quaternary ammonium compounds have been employed in carpets, in U.S. Pat. No. 4,371,577, issued Feb. 1, 1983; applied to walls, added to paints, and sprayed into shoes, in U.S. Pat. No. 4,394,378, issued Jul. 19, 1983; applied to polyethylene surfaces and used in pillow ticking in U.S. Pat. No. 4,721,511, issued Jan. 26, 1988; in flexible polyurethane foams of fine-celled, soft, resilient articles of manufacture in U.S. Pat. No. 4,631,297, issued Dec. 23, 1986; and mixed with a surfactant in Japanese Kokai Application No. 58-156809, filed Aug. 26, 1983, of Sanyo Chemical Industries, Ltd., for the purpose of achieving uniformity of distribution of the compounds to a surface. Thus, the versatility of such compositions is readily apparent. However, no one, as far as is known, has disclosed an organosilicon quaternary ammonium compound attached to a water soluble substrate in accordance with the present invention and having utility as antimicrobially effective agents. The new compositions of the present invention act in preventing microbiological contamination and deterioration, and the new and heretofore undisclosed novel compositions set forth in the present invention possess unique features and advantages over existing antimicrobial treating agents. Thus, the compounds of the present invention may be dissolved in water whereupon the silane responsible for the microbiological activity is released from the water soluble substrate to which it was initially adhered, and is free to adhere to the next available substrate to which the solution is applied or to surfaces immersed therein.

SUMMARY OF THE INVENTION

This invention relates to an antimicrobial water soluble substrate or a substrate formed by a colloidal suspension produced by combining a silane, generically a quaternary ammonium salt form of a silane, with a water soluble powder selected from the group consisting of antiperspirant salts, starches, clays, and sugars. When the substrate is dissolved in water, the silane is released for redeposition. Thus, the treated powders in accordance with the present invention can be dissolved in water, and the solution applied to a substrate where the silane is redeposited from the powder to the substrate. Alternatively, the powder may be sprinkled onto a moistened or wet surface where the silane responsible for the microbiological activity will release from the powder and redeposit and adhere to the moistened or wet substrate to which it has been sprinkled. Typical of water soluble powders are the category of antiperspirant-type salts and agents in powder form, for example, aluminum chlorohydrate and aluminum-zirconium tetrachlorohydrex-glycinate. Other materials which may be used include methyl cellulose; hydroxy ethyl cellulose; sugar such as glucose, fructose, lactose, maltose, and especially sucrose, particularly finely pulverized sugar known as confectioners' sugar; magnesium aluminum silicate; guar gum; colloidal silica; and colloidal clay. There may also be employed a substrate of a mixture of macro cellulose and sodium carboxy methyl cellulose. The treatment level of the silane can be from 0.5 to 2.0 percent by weight based on the weight of the powder, preferably at levels greater than two percent.

It is therefore an object of the present invention to provide an antimicrobial agent that can be applied to substrates to produce an antimicrobial surface having broad spectrum efficacy. In contrast to prior art techniques which have been limited to the application of the agents from aqueous systems to non-water soluble substrates, the present invention involves treatment of water soluble substrates. Once the treated water soluble substrates are dissolved or redissolved in water, the silane agent is released from the water soluble substrate to which it had been adhered, typically a powder, and is available to attach and adhere to another substrate, such as a non-water soluble substrate, rendering it antimicrobial. The non-water soluble substrate could be, for example, a textile or the human underarm area of the skin.

These and other features, objects, and advantages, of the present invention will become apparent from the following detailed description of the invention.

DETAILED DESCRIPTION OF THE INVENTION

Ammonium compounds in which all of the hydrogen atoms have been substituted by alkyl groups are called quaternary ammonium salts. These compounds may be represented in a general sense by the formula:

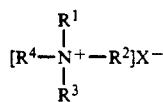

The nitrogen atom includes four covalently bonded substituents that provide a cationic charge. The R groups can be any organic substituent that provides for a carbon and nitrogen bond with similar and dissimilar R groups. The counterion X is typically halogen. Use of quaternary ammonium compounds is based on the lipophilic portion of the molecule which bears a positive charge. Since most surfaces are negatively charged, solutions of these cationic surface active agents are readily adsorbed to the negatively charged surface. This affinity for negatively charged surfaces is exhibited by 3-(trimethoxysilyl)propyldimethyloctadecyl ammonium chloride of the formula:

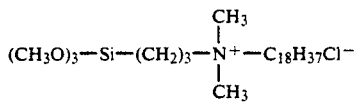

In the presence of moisture, this antimicrobial agent imparts a durable, wash resistant, broad spectrum biostatic surface antimicrobial finish to a substrate. The organosilicon quaternary ammonium compound is leach resistant, nonmigrating, and is not consumed by microorganisms. It is effective against gram positive and gram negative bacteria, fungi algae, yeasts, mold, rot, mildew, and malodor. The silicone quaternary ammonium salt provides durable, bacteriostatic, fungistatic, and algistatic surfaces. It can be applied to organic or inorganic surfaces as a dilute aqueous solution of 0.1-1.5 percent by weight of active ingredient. After the alkoxysilane is applied to a surface, it is chemically bonded to the substrate by condensation of the silanol groups at the surface. The compound is a low viscosity, light to dark amber liquid, soluble in water, alcohols, ketones, esters, hydrocarbons, and chlorinated hydrocarbons. The compound has been used in applications such as, for example, socks, filtration media, bed sheets, blankets, bedspreads, carpet, draperies, fire hose fabric materials, humidifier belts, mattress pads, mattress ticking, underwear, nonwoven disposable diapers, nonwoven fabrics, outerwear fabrics, nylon hosiery, vinyl paper, wallpaper, polyurethane cushions, roofing materials, sand bags, tents, tarpaulins, sails, rope, athletic and casual shoes, shoe insoles, shower curtains, toilet tanks, toilet seat covers, throw rugs, towels, umbrellas, upholstery fiberfill, intimate apparel, wiping cloths, and medical devices.

The compositions of the present invention were prepared in accordance with Examples set forth hereinbelow, and in the Examples as well as in the Tables, the composition identified as TMS refers to a product manufactured by the Dow Corning Corporation, Midland, Mich., as an antimicrobial agent and is 3-(trimethoxysilyl)-propyloctadecyldimethyl ammonium chloride diluted to forty-two percent active ingredients by weight with methanol.

The anion of an aqueous sodium salt of bromphenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromphenol blue is depleted from a standard solution by complexing with the cations on a treated substrate. The change in bromophenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple.

The blank solution is adjusted to yield a 10 to 12% transmittance reading when measured in 1 cm cells using a spectrophotometer set at 589 nm by the following method.

Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, Pa., USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted. The results of this method are reported below.

The silanes useful in this invention have the general formula

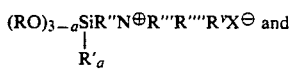

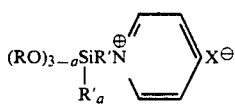

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on Mar. 31, 1981, discusses the use of such silanes to render the surfaces of certain substrates antimicrobial. Canadian Patent No. 1,010,782, issued to Charles A. Roth shows the use of fillers treated with certain silanes to be used in paints and the like to give antimicrobial effects.

Numerous other publications have disclosed such silanes, namely, A. J. Isquith, E. A. Abbott and P. A. Walters, Applied Microbiology, December, 1972, pages 859-863; P. A. Walters, E. A. Abbott and A. J. Isquith, Applied Microbiology, 25, No. 2, p. 253-256, February 1973 and E. A. Abbott and A. J. Isquith, U.S. Pat. No. 3,794,736 issued Feb. 26, 1974, U.S. Pat. No. 4,406,892, issued Sep. 27, 1983, among others.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the ≡SiOH that is formed by hydrolysis of the alkoxy groups present on the silane. The ≡SiOH groups tend to react with the surface and bind the silanes to the surface. It is believed by the inventor even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. In the above formulas RO can also be R. R can also be hydrogen thus indicating the silanol form, i.e. the hydrolyzate. The value of a is 0, 1 or 2 and R' is a methyl or ethyl radical.

R'' for purposes of this invention is an alkylene group of 1 to 4 carbon atoms. Thus, R'' can be alkylene groups such as methylene, ethylene, propylene, and butylene. R''', R'''', and R$^v$ are each independently selected from a group which consists of alkyl radicals of 1 to 18 carbons, —CH$_2$C$_6$H$_5$, —CH$_2$CH$_2$OH, —CH$_2$OH, and —(CH$_2$)$_x$NHC(O)R$^{vi}$. x has a value of from 2 to 10 and R$^{vi}$ is a perfluoroalkyl radical having from 1 to 12 carbon atoms. X is chloride, bromide, fluoride, iodide, acetate or tosylate.

Preferred for this invention are the silanes of the general formula

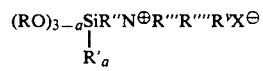

wherein R is methyl or ethyl; a has a value of zero; R'' is propylene; R''' is methyl or ethyl; R'''' and R$^v$ are selected from alkyl groups containing 1 to 18 carbon atoms wherein at least one such group is larger than eight carbon atoms and x is either chloride, acetate or tosylate.

Most preferred for this invention are those silanes having the formula

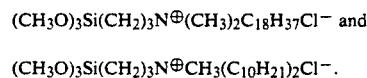

As indicated above, most of these silanes are known from the literature and methods for their preparation are known as well. See, for example, U.S. Pat. Nos. 4,282,366, issued Aug. 4, 1981; 4,394,378, issued Jul. 19, 1983, and 3,661,963 issued May 9, 1972, among others.

Specific silanes within the scope of the invention are represented by the formulae:

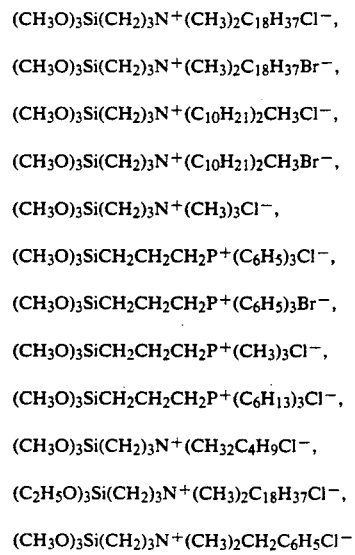

(CH₃O)₃Si(CH₂)₃N⁺(CH₃)₂CH₂CH₂OHCl⁻,

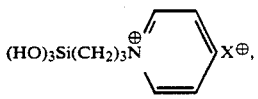

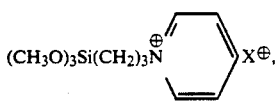

(CH₃O)₃Si(CH₂)₃N⁺(CH₃)₂(CH₂)₃NH-C(O)(CF₂)₆CF₃Cl⁻, (CH₃O)₃Si(CH₂)₃N⁺(C₂H₅)₃Cl⁻.

X is chlorine in the above structures.

EXAMPLE I

Into a flask containing twenty grams of solvent was added one milliliter of TMS, three milliliters of water, and three grams of Powder A(aluminum chlorohydrate). The contents of the flask were mixed and agitated at low heat for twenty to thirty minutes, and filtered. The material was air dried to powder form. The powder was rinsed in anhydrous isopropyl alcohol in order to remove any excess or residual TMS. The rinsed powder was again air dried and subjected to bromophenol blue analysis as outlined previously.

EXAMPLE II

Into a flask containing twenty grams of solvent was added one milliliter of TMS, three milliliters of water, and three grams of Powder B(aluminum-zirconium tetrachlorohydrex-glycinate). The contents of the flask were mixed and agitated at low heat for twenty to thirty minutes, and filtered. The material was air dried to powder form. The powder was rinsed in anhydrous isopropyl alcohol in order to remove any excess or residual TMS. The rinsed powder was again air dried and subjected to bromophenol blue analysis as outlined previously.

EXAMPLE III

Examples I and II were repeated for each solvent system shown in Table I. Thus, a series of sixteen systems were prepared and tested by bromophenol blue analysis; each of the eight solvents being prepared and tested with each one of powders A and B. The data are tabulated in Table I and the results of the bromophenol blue analysis is shown in Table I under the heading "TEST". All of the systems tested positive with the exception of the Powder A-solvent water system. High intensity was manifested by the systems of including the volatile cyclic emulsion, and the solvents isopropanol and toluene with Powders A and B, respectively. Both Powders A and B are water soluble powder forms of antiperspirant agents. All of the powders prepared and tested in accordance with the foregoing procedures and as tabulated in Table I remained water soluble after the preparation and testing procedure. The powders were redissolved in water releasing the TMS, and textile materials immersed therein were rendered antimicrobial by the redeposition of the TMS thereon. The powders were also sprinkled on carpets samples that had been moistened with water and found to be antimicrobial after the carpet samples had been dried and the powder removed by vacuuming, indicating a release of the TMS from the powder and redeposition onto the carpet fiber.

TABLE I

| Solvent (20 gm.) | TMS | Water | Powder A | Powder B | Test |
|---|---|---|---|---|---|
| Water | 1 ml. | 3 ml. | 3 gm. | — | — |
| Water | 1 ml. | 3 ml. | — | 3 gm. | 0 |
| Methanol | 1 ml. | 3 ml. | 3 gm. | — | .+ |
| Methanol | 1 ml. | 3 ml. | — | 3 gm. | + |
| Isopropanol | 1 ml. | 3 ml. | 3 gm. | — | +* |
| Isopropanol | 1 ml. | 3 ml. | — | 3 gm. | 0 |
| Acetone | 1 ml. | 3 ml. | 3 gm. | — | + |
| Acetone | 1 ml. | 3 ml. | — | 3 gm. | + |
| Toluene | 1 ml. | 3 ml. | 3 gm. | — | + |
| Toluene | 1 ml. | 3 ml. | — | 3 gm. | +* |
| Hexane | 1 ml. | 3 ml. | 3 gm. | — | + |
| Hexane | 1 ml. | 3 ml. | — | 3 gm. | + |
| Volatile Cyclic | 1 ml. | 3 ml. | 3 gm. | — | +* |
| Emulsion | 1 ml. | 3 ml. | — | 3 gm. | +* |
| MeOH (No Water) | 1 ml. | — | 3 gm. | — | + |
| MeOH (No Water) | 1 ml. | — | — | 3 gm. | + |

Powder A = aluminum chlorohydrate
Powder B = Al—ZR chlorohydrex-glycinate
Test — = powder remained white
Test 0 = slight blue color
Test + = blue color
Test +* = intense-uniform blue color In Table I, the "volatile cyclic emulsion" is an emulsion where an antimicrobial agent comprised of 3-(trimethoxysilyl)propyloctadecyldimethyl ammonium chloride and 3-chloropropyltrimethoxysilane is the emulsifier, water is the continuous phase, and the discontinuous phase is a volatile silicone of decamethylcyclopentasiloxane.

The antimicrobial activity of a treated surface is evaluated by shaking a smaple weighing 0.75 grams in a 750,000 to 1,500,000 count Klebsiella pneumoniae suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported below as the percent reduction.

Media used in this test are nutrient broth, catalog No. 0003-01-6 and tryptone glucose extract agar, catalog No. 0002-01-7 both available from Difco Laboratories, Detroit, Mich., U.S.A. The microorganism used is Klebsiella pneumoniae American Type Culture Collection; Rockville, Md. U.S.A., catalog No. 4352.

The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second test tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the $10^0$ and $10^{-1}$ dilutions as well as the $10^{-2}$ dilution. "Percent reduction" is calculated by the formula $$\% R = \frac{\frac{B+C}{2} - A}{\frac{B+C}{2}} 100$$

where A is the count per milliliter for the flask containing the treated substrate; B is zero contact time count per milliliter for the flask used to determine "A" before the addition of the treated substrate and C is zero contact time count per milliliter for the untreated control substrate.

EXAMPLE IV

Twenty grams of confectioners' sugar was added to one hundred milliliters of toluene, together with ten grams of TMS. The mixture was stirred for one hour and the liquid was removed by filtration. The particulate was rinsed three times with toluene. The particulate was subjected to bromophenol blue analysis as outlined above, and the percent transmittance determined to be 66.0. The particulate was also evaluated for antimicrobial activity on fabric in accordance the procedure outlined above, and the percent reduction was determined to be one-hundred percent.

It will be apparent from the foregoing that many other variations and modifications may be made in the structures, compounds, compositions, articles of manufacture, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A composition comprising an antiperspirant salt in powder form having chemically bonded thereto an organosilane having the general formula selected from the group consisting of

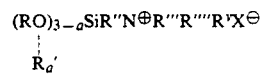

and

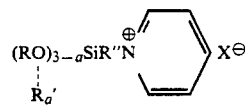

wherein, in each formula,
R is an alkyl radical of 1 to 4 carbon atoms or hydrogen;
a has a value of 0, 1 or 2;
R' is a methyl or ethyl radical;
R" is an alkylene group of 1 to 4 carbon atoms;
R''', R'''' and R$^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and R$^{vi}$ is a perfluoroalkyl radical having from 1 to 12 carbon atoms; and
X is chloride, bromide, fluoride, iodide, acetate or tosylate.

2. A composition as claimed in claim 1 wherein the organosilane has the formula

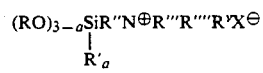

wherein R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and R$^{vi}$ is a perfluoroalkyl radical having from 1 to 12 carbon atoms; X is chloride, bromide, fluoride, iodide, acetate or tosylate.

3. A composition as claimed in claim 1 wherein the organosilane has the formula

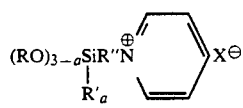

wherein R is an alkyl radical of 1 to 4 carbon atoms or hydrogen; a has a value of 0, 1 or 2; R' is a methyl or ethyl radical; R" is an alkylene of 1 to 4 carbon atoms; X is chloride, bromide, fluoride, iodide, acetate or tosylate.

* * * * *